United States Patent [19]
Knüttel

[11] Patent Number: 5,565,986
[45] Date of Patent: Oct. 15, 1996

[54] STATIONARY OPTICAL SPECTROSCOPIC IMAGING IN TURBID OBJECTS BY SPECIAL LIGHT FOCUSING AND SIGNAL DETECTION OF LIGHT WITH VARIOUS OPTICAL WAVELENGTHS

[76] Inventor: Alexander Knüttel, Brunhildstr. 39, 69469 Weinheim, Germany

[21] Appl. No.: 405,299

[22] Filed: Mar. 16, 1995

[30] Foreign Application Priority Data

Mar. 30, 1994 [DE] Germany .......................... 44 11 017.0

[51] Int. Cl.$^6$ ...................................................... G01B 9/02
[52] U.S. Cl. ............................................ 356/346; 356/345
[58] Field of Search ...................................... 356/346, 345

[56] References Cited

U.S. PATENT DOCUMENTS 3,702,735 11/1972 Potter ....................................... 356/346
5,192,980 3/1993 Dixon et al. ............................. 356/346

Primary Examiner—Frank Gonzalez
Assistant Examiner—Amanda Merlino
Attorney, Agent, or Firm—Walter A. Hackler

[57] ABSTRACT

Interferometer apparatus includes a light source, disposed in a light source arm, for emitting light at various wavelengths and a focusing device disposed in an object arm for focusing the emitted light simultaneously into at least two different regions within an object, the focused light being reflected from the object. A reference is provided, including a reflective element, for reflecting light from the light source means and a detector, disposed in a detector arm is provided for measuring different wavelengths of the light reflected from the reference means and the object, in order to obtain a spectroscopic image of the object, displaying both spacial resolution in a lateral direction and a field of view in a depth direction.

24 Claims, 2 Drawing Sheets

STATIONARY OPTICAL SPECTROSCOPIC IMAGING IN TURBID OBJECTS BY SPECIAL LIGHT FOCUSING AND SIGNAL DETECTION OF LIGHT WITH VARIOUS OPTICAL WAVELENGTHS

This invention relates to an apparatus of an interferometer type for optical spectroscopical imaging with at least one-dimensional spatial resolution in turbid objects, like biological objects or polymers, with a light source in a source arm to radiate light with various wavelengths, with a device to split light into a sample arm and a reference arm, while light in the sample arm is focused on various preselected regions in an object under investigation, the light beams are reflected from the object and the reference element and, after recombination, guided towards a detector unit in the detector arm to measure the interfering light beams, with said apparatus employing no mechanically moving, utmost in the sub-µm range vibrating, parts.

Such an optical interferometer is known from a paper of A. Knüttel et al. OPTICS COMMUN. 102 (1993) p. 193–198.

Turbid objects are generally opaque objects which scatter light off an optical axis to a certain extent. Obviously these objects include all biological objects and many polymers (plastics). Even though the eye is the least opaque biological object, it is not as transparent as for e.g. a high quality optical lens. Optical spectroscopic imaging in turbid objects can be employed to characterize these media via different optical parameters. Established methods, like confocal microscopy, are restricted to regions close to surfaces of turbid objects, because undesired stray light begins to overwhelm the desired (nearly) diffraction-limited signal contribution in depths exceeding few 10 µm (Nearly) diffraction-limited signal means that only (almost) unscattered photons contribute to the signal. Many optical methods based on low-coherence or short-coherence interferometry exist, which exploit the desired unscattered signal photons. The common working principle can be briefly summarized as follows: Light emanating from a (broadband) source in the source arm is split by a beam splitter and launched into an object arm and a reference arm. Each arm is terminated by an object under investigation and a reference mirror, respectively. The reflected light beams from both arms are recombined in the same beam splitter and guided towards a detector in the detector arm, which can measure an interference signal. The occurance of an interference signal depends on the pathlength conditions of both interferometer arms; it occurs when the difference between both optical pathlengths is (almost) zero. The uncertainty in said difference pathlength, which defines depth resolution, is determined by the coherence length of a broadband light source. Typical coherence lengths are about 10–50 µm. In low-coherence interferometry partially coherent light sources like LED's or SLD's are employed while in short-coherence interferometry mode-locked lasers produce light with short coherence lengths. Principle advantages of interferometry are accurate spatial selection in depth direction (due to the broad wavelength spectrum) and very high signal sensitivity.

To obtain spatial information in depth direction of a turbid object (for 1D imaging) usually a mirror in the reference arm of an interferometer is moved mechanically, as known from Takada et al., APPLIED OPTICS, Vol. 26, No. 9 (1987) p. 1603–1606 and Swanson et al., OPTICS LETTERS, Vol. 17, No. 2 (1992) p. 151–153. Typical ranges for mechanical displacements in the reference arm are on the order of 1 mm.

To further enhance the spatial selection capabilities with regard to imaging, light is focused into the object to define a region of high photon density in and close to the focus spot. The focal region is defined in the following as region where the photon density stays above ½ of the maximum photon density in the center of the focal region. The choice of the numerical aperture of a lens or an objective determines the extent of a focal region. Tighter focus (high numerical aperture) improves lateral resolution (smaller focus region) but also limits the range along depth direction from which sufficient reflected signal of the object can be detected. Outside this said region the signal efficiency drops rapidly. In order to cover a large depth range, the numerical aperture has to be reduced with consequently decreased resolution. This trade-off has to be met by all currently existing imaging devices.

For spectroscopic information without spatial resolution (without imaging), an object is positioned either in the source or detector arm of an interferometer. The object and reference arms are terminated with mirrors with one of them mechanically moved. The movement range can cover up to several cm's to retrieve high spectral wavelength resolution. This is the basic principle of commercial spectrometers.

A stationary interferometer (no mechanical parts) for imaging purposes is known from the above mentioned paper of A. Knüttel et al. In the described setup each spatial point in depth dimension is mapped onto a particular element of a one-dimensional detector array with extent in lateral direction. Each particular element detects all wavelengths of the broadband light source simultaneously. A drawback of this method is that it is not too efficient when only few points along depth direction, with the corresponding elements of the array, are addressed because all other elements have to be ignored.

Stationary interferometers for spectroscopic purposes without imaging capabilities are known from for e.g. Junttila et al., J. OPT. SOC. AM., Vol. 8, No. 9 (1991) p. 1457–1462, Okamoto et al., APPLIED OPTICS, Vol. 23, No. 2 (1984) p. 269–273. As in commercial spectrometers the objects under investigation are placed either in the source or detector arms of the interferometer, implying that a spatial selection is not possible (because light from the sample and reference arm impinges on the object).

There is accordingly a need for an apparatus to obtain data particularly from turbid objects and to extract spectroscopic features combined with imaging, to form a spectroscopic image.

There is a specific need for an apparatus to perform imaging with high resolution in lateral directions yet covering a large field of view in depth direction without severe signal loss.

There is a particular need for an apparatus to obtain high signal efficiencies even when only few regions in depth direction are addressed.

There is a more particular need for an apparatus to obtain data in a stationary manner, which can include vibrating parts in sub-µm range, to facilitate operation on in harsh clinical environments.

SUMMARY OF THE INVENTION

It is accordingly an object of the present invention to provide an apparatus which combines spectroscopy and imaging capabilities.

It is a more specific object of the invention to permit high spatial resolution in lateral dimension while covering a large field of view in depth direction without severe penalty by signal loss.

It is particularly an object of the invention to obtain high signal efficiencies even when only few region along depth direction are addressed.

It is more particularly an object of the invention to provide an apparatus to obtain data without moving pans or only vibrating pans in the sub-μm range.

In accordance with these and other objects of the present invention, there is provided an apparatus working in stationary mode to detect various optical wavelengths separately and light focusing is performed into different preselected depth regions. The various optical wavelengths are detected either by spatially separated detector elements simultaneously at any given time or by one detector element in a time-sequential manner. Light with a given optical wavelength of the spectrum is focused simultaneously into the different preselected depth regions.

The various optical wavelengths from the spectrum can be detected in different ways. Three different embodiments of the invention are listed:

1) The broadband light guided towards the detector unit is first spectrally dispersed, by for e.g. an optical grating, and the individual spectral components are detected simultaneously (in time) with spatially separated detector elements of an array.

2) The light source is spectrally tunable and emits monochromatic light (for e.g. a laser diode) or spectrally very smallband light (for e.g. a special superluminescent diode, SLD) at any instant in time. The light is launched into the interferometer and detected with one detector. There are two ways of spectral tuning with corresponding signal processing: a) the wavelength spectrum is ramped through in steps which is described by Hotate et al., SPIE PROCEEDINGS, Vol. 1586 (1991) p. 32–45 and b) the wavelength spectrum is ramped through continuously as known for e.g. from U.S. Pat. No. 3,647,298. These published embodiments employ interferometers as well but no spectral imaging was performed and no device for simultaneous light focusing into various regions of an object is demonstrated.

3) Light propagating in one of the four interferometer arms (defined by the four terminating elements: light source, detector unit, object, reference element) is time sequentially coded by a device, detected with one detector element and data processed afterwards. The said device, which is under electronic control, consists of dispersive elements and a flat multi-pixel mask (for e.g. Hadamard mask with liquid crystals). Each pixel can either modulate the amplitude or phase or both of the corresponding light wave. Hadamard masks are well known from Vickers et al., APPLIED SPECTROSCOPY, Vol. 45, No. 1 (1991) p. 42–49 or Liu et al., APPLIED SPECTROSCOPY, Vol. 45, No. 10 (1991) p. 1717–1720. For each of these published embodiments no device for simultaneous light focusing into various regions of an object exists.

In accordance with the above listed embodiments 1), 2) and 3) or a combination of them, the apparatus of the invention employs a device for simultaneous light focusing into different regions in the object. Such device acts as a superposition of individual lenses or objectives with individual (but different) focal lengths. According to the different focal lengths, light is focused into various different focal regions. Various different focal regions can be addressed simultaneously mainly along depth direction. Thus high spatial resolution in lateral directions can be combined with large probing range in depth direction. Individual (noncontiguous) focal regions can be addressed as well.

In accordance with the invention, spectroscopic optical parameters can be assigned to each point within an image. To explain the procedure for feature extraction, two signals from two different depth regions in an object are assumed to exhibit different backscattered signals due to for e.g. absorption. By taking the difference of these signals and the exact knowledge of the two depth regions (spatial selection), optical parameters for the corresponding spacial regions can be extracted. By choosing a very short spatial difference distance a detailed map of spatially distributed spectroscopic parameters (for e.g. absorption) along depth direction can be obtained. By adding lateral scanning a two-dimensional (2D) spectroscopic map, which is a spectroscopic image, can be obtained. Optical parameters, which can be wavelength-dependent, include for e.g. the complex refractive index (real part is the refractive index and the imaginary part the absorption), the state of polarization and the scattering coefficient. It is known that a combination of these parameters leads to further known (more complex) ones, like for e.g. the circular dichroism (CD).

A special embodiment of the invention contains an interferometer type according to Michelson. In accordance to the broad aspects of the invention also other interferometer types can be employed, for e.g. Mach-Zehnder types.

In one embodiment of the invention, two-dimensional (2D) spectroscopic imaging can be obtained according to embodiment 1), where a 2D detector array is employed. One dimension of the array is used for spatial selection in depth direction, while the other dimension covers one lateral direction.

In another embodiment of the invention, 2D spectroscopic imaging can be obtained according to the embodiments 2) and 3), where a 1D detector array is employed. The one dimension of the array covers one lateral direction.

To extend the dimensionality in imaging to 2 dimensions, a special embodiment of the invention contains a light source which is spatially extended in one dimension. The said light source can contain a continuous array of light sources or a discrete array with all sources emitting light simultaneously.

In a further embodiment of the inventive apparatus, three-dimensional (3D) spectroscopic imaging can be conducted according to the embodiments 2) and 3), where a 2D detector array is employed. Each element of the array is used for depth selection (in a time-sequential manner) while the 2 dimensions are reserved for the spatial directions.

To extend the dimensionality in imaging to 3 dimensions, a special embodiment of the invention contains a light source which is spatially extended in two dimensions. The said light source can contain a continuous array of light sources or a discrete array with all sources emitting light simultaneously.

In accordance with the invention, a data processing method can reduce the dimensionality of the obtained images to average out local fluctuations and to enhance signal-to-noise ratio (S/N). For e.g. in a 2D image all depth scans along lateral positions can be averaged together to obtain one depth scan with smoothed signal profile.

In accordance with the broad aspects of the invention, a preferred embodiment of the apparatus employs a device to periodically phase modulate the light in one of the interferometer arms, preferentially in the reference arm. Consequently the detected interference signals are AC modulated which permits best S/N due to suppression of undesired DC background-signal components. Different embodiments to perform said phase modulation apply.

In one embodiment of the invention, the phase modulation can be performed with a pattern mask, as described in embodiment 3), since each element of the pattern mask can vary electronically the phase of the transmitting light.

In another embodiment, a reflecting element in the reference arm vibrates periodically with a maximum range of typically sub-μm. Periodic means in this context that the way the vibration is done is repetative, but the waveform can be arbitrary. For e.g. the reflecting element can be attached to a piezo-electric transducer, which can vibrate typically in the kHz frequency range. Such a device is still refered to as stationary, since periodical vibrations in the sub-μm range are too small to affect system stability (as comparison, unavoidable temperature fluctuations of few °C. can cause changes in optical pathlength of similiar order).

In again another embodiment, a non-vibrating device for phase modulation can be disposed in one arm of an interferometer, preferentially in the reference or sample arm. Such a device can be an acousto-optic modulator, which shifts the phase of the light periodically to cause a constant frequency offset. The said frequency offset ranges typically in the region around few 10 MHz. By combination of at least two acousto-optic modulators (assembly), a difference frequency on the order of kHz can be generated, which is state of the an. Signal frequencies in the kHz region are easier to detect than in the MHz region.

In accordance with all aspects of the invention, light propagating in the object arm is focused simultaneously into different regions, preferentially along depth direction. Simultaneous focusing is advantageous, since probing the full depth range or various (noncontiguous) depth regions can be performed while retaining high lateral resolution.

In another embodiment optical diffracting devices, like for e.g. holographic zone plates, can be employed. Different orders of diffraction can be exploited to focus light into different regions along depth direction. The said zone plates can be computer generated.

In a preferred embodiment an assembly of optical elements can create the multiple focus regions. In a particularly preferred embodiment, one refractive element, for e.g. a glass lens, can be combined with a diffractive zone-plate. Such an assembly can minimize optical (for e.g. chromatical) aberrations.

In a special embodiment of the focusing device, the various focus regions can partially overlap to obtain effectively one extended focal region. This embodiment is interesting when the desired depth range fits within the said extended focal region. This is in accordance with the broad aspects of the invention.

In a particularly preferred embodiment, the complete interferometer, except the focusing device, can be incorporated in integrated optics and/or micro-optics. The compact size and robustness will have advantages for clinical applications.

In a further improved embodiment, the complete interferometer, including focusing device, can be incorporated in integrated optics and/or micro-optics with similiar advantages.

In another embodiment including all aspects of the invention, each element of the detector array, the signal amplitudes of each spectral component of the light and/or each element of the electronic pattern mask can be calibrated. In one embodiment, a non-mechanical shutter (for e.g. liquid crystal) disposed in the object arm of the interometric apparatus permits light to be launched periodically with alternating intensities into the object. In the period where no light is reflected from the object, the spectral components from the light signal of the reference arm can be calibrated. The said calibration can be important for absolute quantification of the various spectral components when the detected spectral signal component varies in intensity even without object.

A preferred embodiment of all aspects of the invention can be the employment of the apparatus as coherent Raman spectrometer. The optical frequency (which can be convened to wavelength) of the coherently Raman-shifted line from the object in the object arm can be detected when a measurable difference frequency compared to the optical frequency of the (not Raman shifted) signal of the reference arm occurs. The said difference frequency can be in the GHz range, which would correspond to small Raman shifts. Exceeding about 100 GHz becomes technologically difficult at the present state of the art. In this embodiment the advantage is the selective detection of a very small Raman line compared to a Raleigh line (not frequency shifted) with corresponding suppression of the undesired Raleigh line. In commercial Raman spectrometers the adjacent Raman line is often burried in the, "wings" of the Raleigh line, particularly when the frequency difference is small (GHz region), because the only option to suppress the Raleigh line is by means of optical filtering. Of course this option can be employed in the present inventive apparatus as well.

It is obvious that the mentioned embodiments are not restricted to stand alone versions but can be employed in any combination as well without leaving the aspects of the invention.

BRIEF DESCRIPTION OF THE DRAWINGS

In the following the invention is described with regard to the presented embodiments in the drawings.

It is shown.

DETAILED DESCRIPTION

Figure 1:
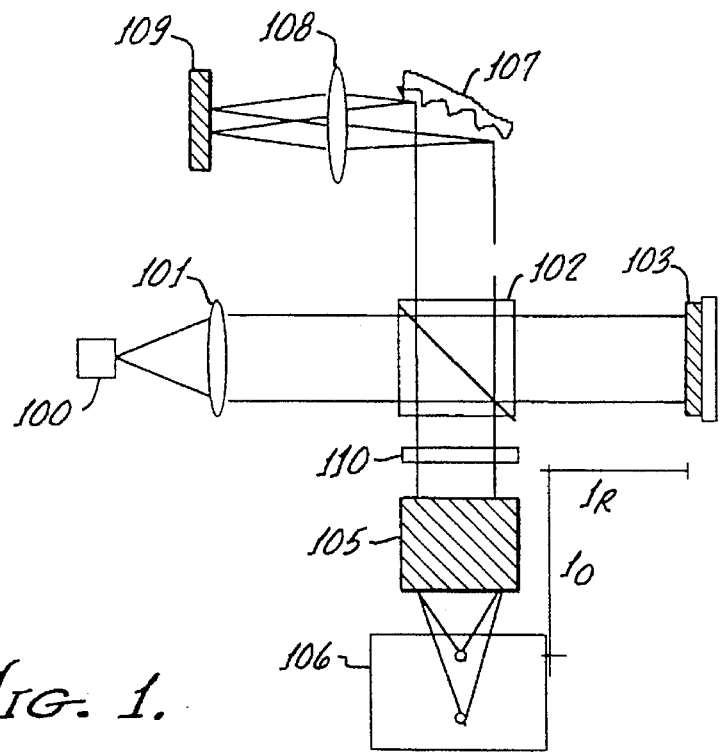
FIG. 1: a first embodiment of the inventive optical apparatus.

An embodiment of a stationary interferometer for 1D spectroscopic imaging is shown in FIG. 1 for parallel detection of the various spectral parts by a 1-dimensional detector array. The light source (100) emits light with a broadband spectrum. Light is collimated by a lens or an objective (101) and split by a beamsplitter (102) into an object arm and a reference arm. Light in the object arm is focused by a focusing device (105, for details see FIG. 4) into an object (106). The reference arm is terminated by a mirror (103) mounted on a vibrating element (104). After reflection from the object (106) and the mirror (103) the light is recombined in the beamsplitter (102) and launched into a dispersive element like a grating (107) for spatial separation of the spectral components. The individual elements of the detector array (109) simultaneously detect the spectral light components (various wavelengths) after being focused by a lens or an objective (108). Thus in one scan the full depth information is accessible. Optionally, in the object arm an electrical shutter (110) can be disposed to temporarily block light from the object which serves calibration of the light from the reference arm.

According to eq. (1), the information obtained from the detector array (109) can be exploited for spectral imaging. The measured phase difference $\Delta\phi$ per detector element $$\Delta\phi = 2\pi(l_o - l_R) n(\lambda)/\lambda \tag{1}$$

is dependent on the optical difference path $(l_o - l_R)n(\lambda)$ and the wavelength $\lambda$. For imaging purposes the reference pathlength $l_R$ is kept constant while the pathlength in the object arm $l_o$ changes due to various penetration depths in the object itself. The refractive index $n(\lambda)$ can be wavelength dependent. Due to the dispersive element (107) the spectral components (with the corresponding amplitude and phase informations) are directed wavelength dependent towards the elements of the detector array (109). At a given optical path difference and refractive index the phase rises (or falls) linearly with the wavelength (within a to small region) along the detector array. According to the known interferometric cross correlation term, a linear phase ramp produces a sinusoidal amplitude variation along the detector array (109) which in turn can be assigned to a spatial frequency. With regard to imaging, and at fixed refractive index, any given optical path difference is transformed via Fast Fourier Transformation (FFT) into a discrete spatial frequency. The ensemble (sum) of various penetration depths (corresponding to various differences in optical pathlengths) produces a spatial frequency spectrum which corresponds to a information signal profile obtained by an interferometer with moving reference mirror. The same procedure applies for spectroscopic imaging as well.

A spectroscopic 1-D image (along depth direction) is obtained as follows. For a moment assuming that light is only focused simultaneously into two different regions (along depth) of the turbid object, two corresponding signal profiles are obtained after FFT whose maxima contribute to the spatial information. The spectral informations (of both regions) are contained in variations of signal profiles (along depth within each focus region). Data processing of these two signal profiles (like ratioing or subtracting) yields an optical parameter between the two spatial regions. An optical parameter like for e.g. the absorption coefficient can be derived according to Beers' law, since the distance between the two spatial regions is known. Spectral information, like for e.g. (complex absorption), can be wavelength dependent. With light from more than two depth regions a 1D spectroscopic image can be obtained, with decreasing distances between two adjacent regions. The spectroscopic dimension is not assigned seperately (it is still a 1D spectroscopic image).

For multidimensionale spectroscopic images the above described procedure is repeated for each point along the lateral directions. For 2D and 3D spectroscopic images, one and two lateral dimensions, respectively, have to be covered.

Figure 2:
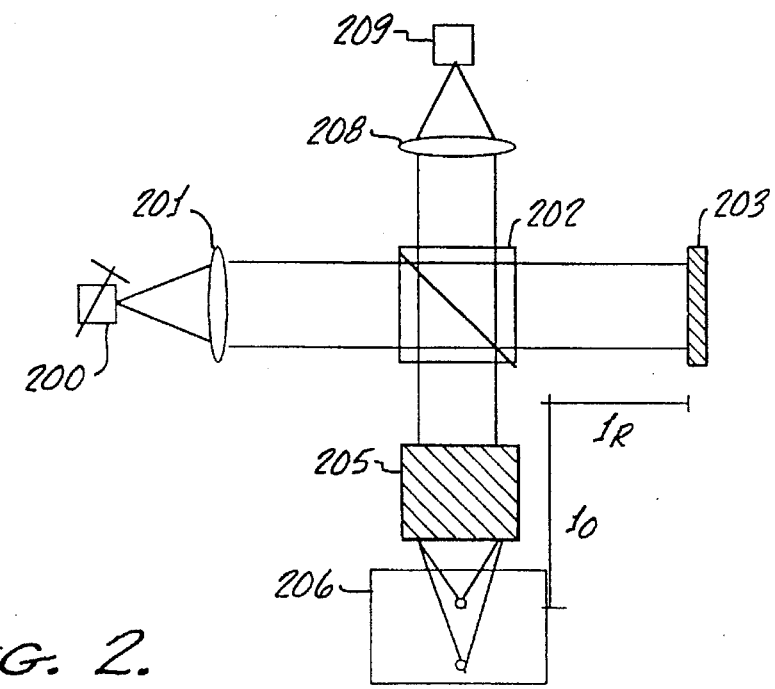
FIG. 2: a second embodiment of the inventive optical apparatus.

A second embodiment of a stationary interferometer is shown in FIG. 2 in which the various spectral components of the light are detected in a time-sequential manner using a tunable light source (200) and a single detector element (209). The light source (200), emitting light with a very smallband or even monochromatic spectrum, is tunable, as indicated by the tilted bar. Light is collimated by a lens or an objective (201) and split by a beamsplitter (202) into an object arm and a reference arm. Light in the object arm is focused by a focusing device (205, for details see FIG. 4) into an object (206). In the reference arm light is reflected from a mirror (203) in fixed position. After reflection from the object (206) and the mirror (203) the light is recombined in the splitter (202) and guided via focussing lens or objective (208) to the single detector element (209).

As described for FIG. 1, spatial frequencies, retrieved from a detector array, are assigned to depth regions within an object. For the approach according to FIG. 2, temporal instead of spatial frequencies are assigned to depth regions. The temporal frequencies are retrieved from a single element detector. Two operational modes can be chosen. Both produce the same final result but the approach to tune the light source is different.

In the first mode, the various wavelengths are tuned in discrete steps and the desired depth information can be obtained in a process analogous to the one described for FIG. 1. As long as the measurement time per wavelength is long compared to the time-of-flight of the light in the object, no transient perturbation effects are expected.

In the second mode, the wavelength spectrum is tuned through in a continuous manner. In other words, a plot wavelength vs. time would exhibits a linear ramp. As described above for FIG. 1, spatial frequencies are assigned to depth positions via the mathematical procedure FFT. Here the temporal frequencies are obtained directly from the wavelength ramping according to $$f_D = \Delta\lambda/\Delta t \ 2(l_o - l_R)n(\lambda)/\lambda_o^2, \tag{2}$$

while no FFT is necessary. Eq. (2) was derived from Suematsu et al., APPLIED OPTICS, Vol. 30, No. 28(1991) p. 4046–4055. The rate to ramp the wave-length with time is denoted by $\Delta\lambda/\Delta t$.

Figure 3:
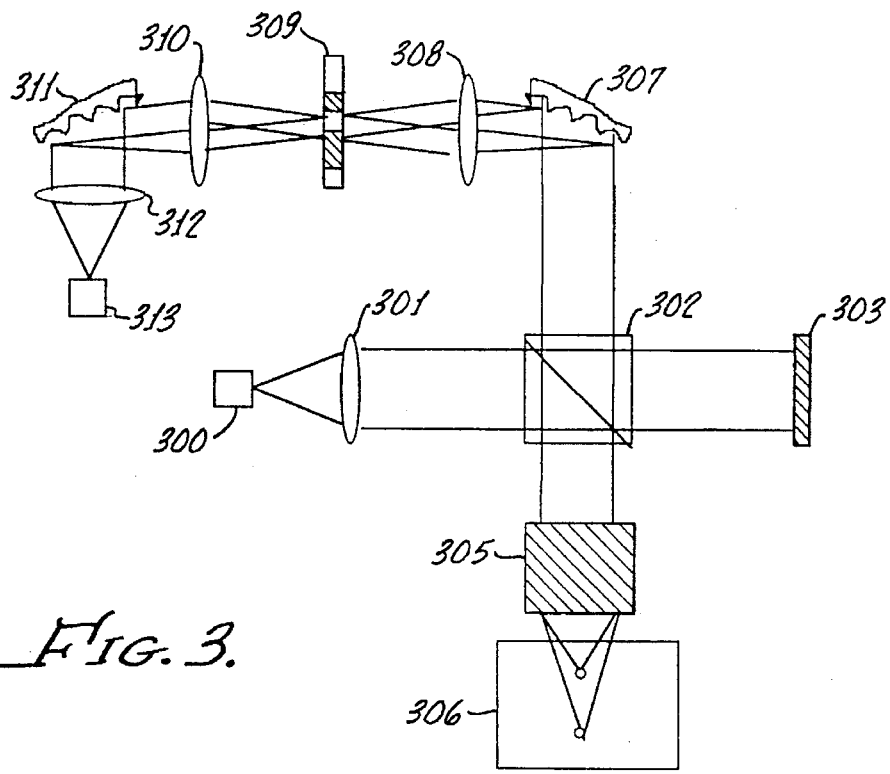
FIG. 3: a third embodiment of the inventive optical apparatus.

A third embodiment of a stationary interferometer is shown in FIG. 3. Various spectral components from a broadband light source (300) are transmitted in a time sequential manner via an electronic mask and subsequently detected by a single detector element (313). Broadband light from the source (300) is collimated by a lens or an objective (301) and split by a beamsplitter (302) into an object arm and a reference arm. Light in the object arm is focused by a focusing device (305, for details see FIG. 4) into an object (306). In the reference arm light is reflected from a mirror (303) in fixed position. After reflection from the object (306) and the reference mirror (303) the light beams are recombined in the beam splitter (302) and guided towards the first dispersive element (307). The spatially dispersed light is focused by a lens or an objective (308), it propagates through an electronically controlled mask (309) and is recollimated by a lens or an objective (311). The effect of spectral dispersion in the dispersive element (307) is reversed by a second dispersive element (311). The (undispersed) light is focused via lens or objective (312) onto the single element detector (313). The mask can be controlled electronically in various ways to obtain signal profiles (along depth direction) as described above. One (trivial) approach to control the mask is to sequentially permit one spectral component at a time to transmit through device (309). This is similiar to the step-wise tuning of a light source and thus the function of this approach is obvious, according to the text for FIG. 2).

Figures 4A, 4B:
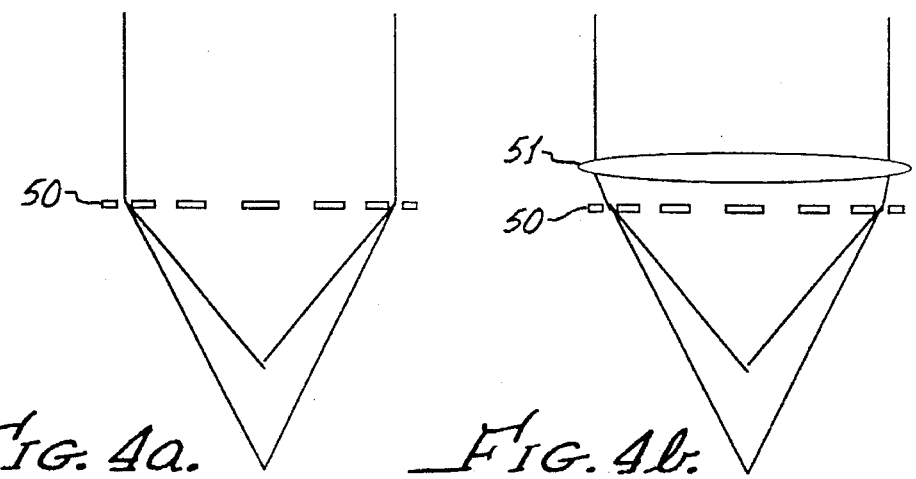
FIG. 4: two embodiments of a focusing device of the inventive apparatus utilizing a) a holographic zone plate, and b) a combination of a lens or objective with a holographic zone plate, to produce two depth focusing regions within an object.

In FIG. 4a) a particularly simple version of a focusing device is shown, comprising only a holographic plate (50).

In FIG. 4b) a prefered version of a focusing device is shown, comprising a lens or and objective (51) and a holographic plate. These devices enable the simultaneous focusing of light in the object arm (not shown in FIG. 4) into two different regions of an object, as illustrated by the converging lines.

Figure 5:
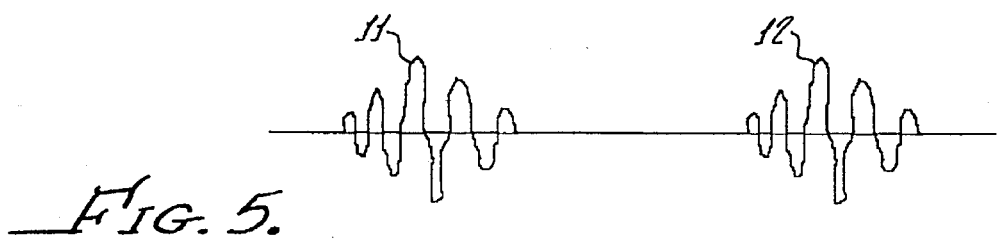
FIG. 5: typical example of data retrieved after mathematical manipulation (usually Fast Fourier Transformation) from signals collected simultaneously from two different preselected depth regions.

In FIG. 5 a typical example of a depth profile obtained from two depth regions is shown. The maxima of the already processed signal profiles (11, 12) contribute to the spatial information, while the signal variations contribute to the spectral informations.

I claim:

1. Interferometer apparatus for performing spectroscopic imaging, said apparatus comprising:

light source means, disposed in a light source arm, for emitting light at various wavelengths;

focusing means, disposed in an object arm, for focusing the emitted light simultaneously into at least two different regions within an object, the focused light being reflected from the object;

reference means, including a reflective element, for reflecting light from the light source means; and detector means, disposed in a detector arm, for measuring different wavelengths of the light reflected from the reference means and the object, in order to obtain a spectroscopic image of the object, displaying both spacial resolution in a lateral direction and a field of view in a depth direction.

2. The interferometer apparatus according to claim 1 further comprising area pixel mask means, disposed in one of the arms, for electronically encoding the emitted light in order to transmit spectral components of the emitted light in a time sequential manner.

3. The interferometer apparatus according to claim 2 wherein said area pixel mask means includes means for modulating the phase of the emitted light.

4. The interferometer apparatus according to claim 2 wherein said area pixel mask means includes means for modulating the amplitude of the emitted light.

5. The interferometer apparatus according to claim 1 further comprising means, including at least one dispersive element disposed adjacent the detector means, for causing spectral dispersion of light entering the detector means.

6. The interferometer apparatus according to claim 1 wherein the detector means is adapted for detecting light in one dimension, and wherein the light source means is spatially extended in one dimension, in order to enable two dimensional spectroscopic imaging of the object.

7. The interferometer apparatus according to claim 1 wherein the detector means is adapted for detecting light in two dimensions, and wherein the light source means is spatially extended in two dimensions, in order to enable three dimensional spectroscopic imaging of the object.

8. The interferometer apparatus according to claim 1 further including means, disposed in one of the arms, for modulating the phase of light in order to suppress DC background signals of the light entering the detector means.

9. The interferometer apparatus according to claim 8 wherein the means for modulating the phase of light comprises means, disposed in the reference arm, for causing the reflective element to periodically vibrate.

10. The interferometer apparatus according to claim 8 wherein the means for modulating the phase of light comprises non-vibrating means for periodically phase modulating the light.

11. The interferometer apparatus according to claim 10 wherein the non-vibrating means includes an acousto-optic modulator.

12. The interferometer apparatus according to claim 1 wherein the focusing means comprises at least one diffractive element.

13. The interferometer apparatus according to claim 12 wherein the focusing means further comprises at least one refractive element.

14. The interferometer apparatus according to claim 1 further comprising electronically controlled light shutter means, disposed in the object arm, for enabling calibration of spectral components during a period when no light is reflected from the object.

15. Interferometer apparatus for spectroscopic imaging, said interferometer apparatus comprising:

a source arm, including means for emitting a beam of light;

an object arm;

a reference arm, adapted for including a reflective element therein;

means for splitting the beam of emitted light, and directing one portion of the emitted light into the object arm and directing another portion of the emitted light into the reference arm;

focusing means, disposed within the object arm, for focusing the light simultaneously into at least two different depth regions within an object;

means for causing light reflected from the object arm and the reference arm to be recombined;

detector means for measuring spectral components of the recombined light, so that at one scan of the object, a spectroscopic image of the object yields both spacial resolution in a lateral direction and a field of view in a depth direction.

16. The interferometer apparatus according to claim 15 further comprising area pixel mask means, disposed in one of the arms, for electronically encoding the light in order to transmit spectral components of the emitted light in a time sequential manner.

17. The interferometer apparatus according to claim 15 further comprising means, disposed in one of the arms, for modulating the phase of light in order to suppress DC background signal components of light entering the detector means.

18. The interferometer apparatus according to claim 15 wherein said focusing means comprises at least one diffractive element.

19. The interferometer apparatus according to claim 18 wherein said focusing means further comprises at least one refractive element.

20. A method for performing spectroscopic imaging comprising the steps of:

emitting a beam of light from a light source;

causing the beam of light to be split into an object arm and a reference arm;

focusing the light in the object arm simultaneously into at least two depth regions of an object;

reflecting the light from both a reflective element in the reference arm and from said object, so that the light is recombined;

directing the recombined light into a detector arm; and measuring spectral light components of the light in the detector arm, so that at one scan of the object, a spectroscopic image of the object yields both spacial resolution in a lateral direction and a field of view in a depth direction.

21. The method according to claim 20 further comprising the step of electronically encoding the emitted light in order to transmit spectral components of the emitted light in a time sequential manner.

22. The method according to claim 20 wherein the step of focusing comprises the step of guiding the light through a diffractive element in order to create multiple focus regions within the object.

23. The method according to claim 22 wherein the step of focusing further comprises the step of guiding the light through a refractive element.

24. The method according to claim 20 further comprising the step of dispersing the recombined light entering the detector arm, and the step of measuring comprises simultaneously detecting individual spectral components of the dispersed light.

* * * * *